United States Patent [19]

Dedo

[11] Patent Number: 5,180,359
[45] Date of Patent: Jan. 19, 1993

[54] CAST PADDING

[76] Inventor: Richard G. Dedo, 175 Denise Dr., Hillsborough, Calif. 94010

[21] Appl. No.: 252,742

[22] Filed: Oct. 3, 1988

Related U.S. Application Data

[63] Continuation of Ser. No. 890,555, Jul. 30, 1986, abandoned.

[51] Int. Cl.⁵ .................................................. A61F 5/04
[52] U.S. Cl. ........................................ 602/6; 602/20; 602/23; 602/62
[58] Field of Search ....................... 128/82, 82.1, 87 R, 128/87 A, 89 R, 89 A, 90, 91 R, 77, 165, 166, 169, 155, 156, 85

[56] References Cited

U.S. PATENT DOCUMENTS

| | | |
|---|---|---|
| 2,980,110 | 4/1961 | Brumfield et al. ................. 128/87 R |
| 3,255,748 | 6/1966 | Wallerstein . |
| 4,129,127 | 12/1978 | Ellison ............................... 128/91 R |
| 4,143,653 | 3/1979 | Wichman ........................... 128/87 A |
| 4,381,769 | 5/1983 | Prahl . |
| 4,409,972 | 10/1983 | Prahl . |
| 4,479,490 | 10/1984 | Dedo . |
| 4,532,922 | 8/1985 | Golyakhovsky ................. 128/91 R |

FOREIGN PATENT DOCUMENTS 629745  10/1961  Canada ............................. 128/89 R Primary Examiner—Danton D. DeMille
Attorney, Agent, or Firm—Powell Sprunger; John Schipper

[57] ABSTRACT

An article for use in making a cast on a patient comprising, an elongated strip of porous material having a base portion and a raised edge portion extending from a line of juncture with the base portion.

15 Claims, 4 Drawing Sheets

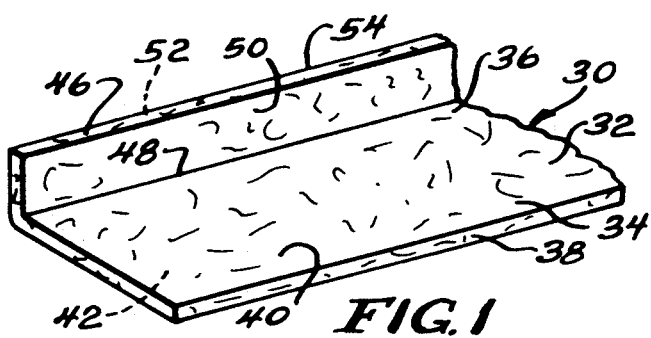
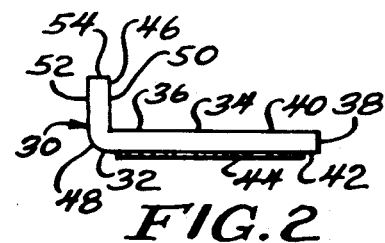
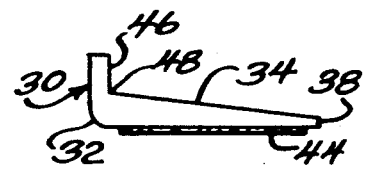
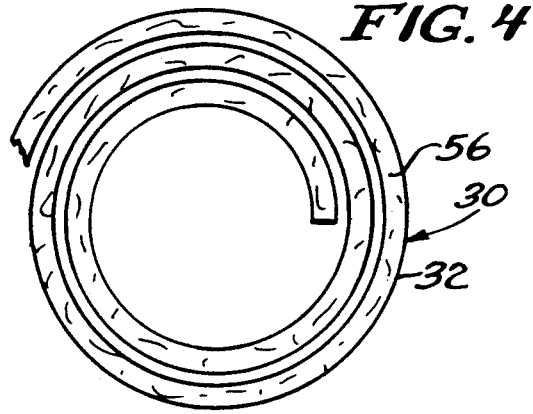
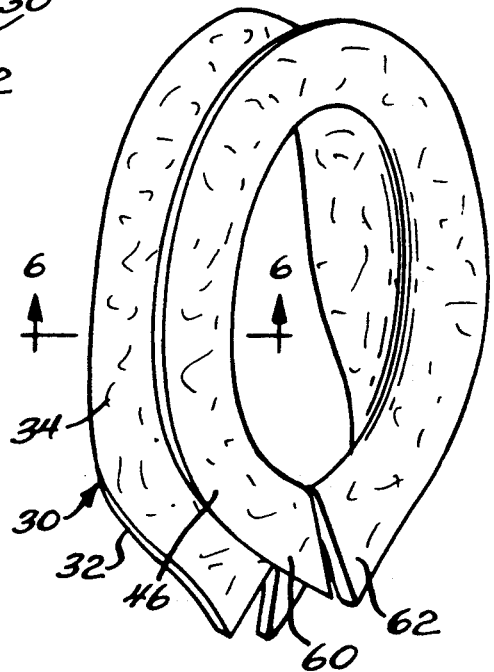
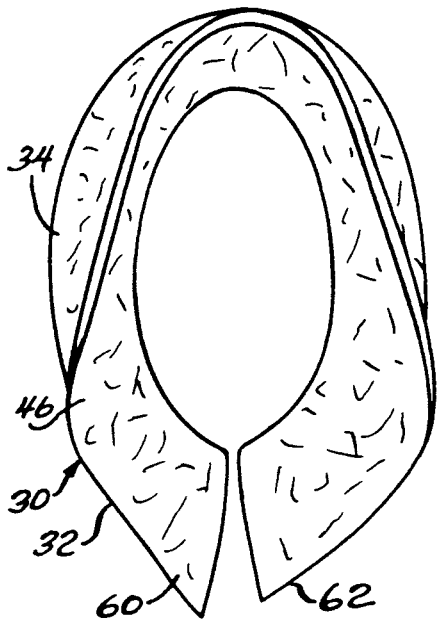
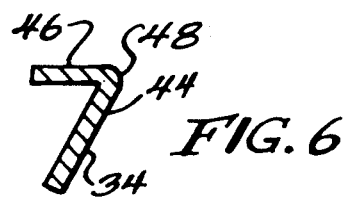

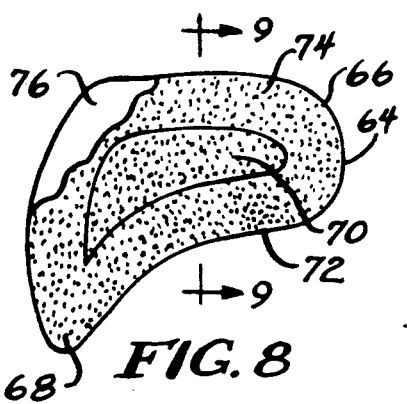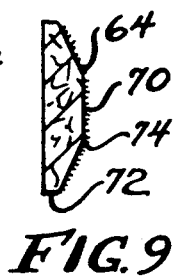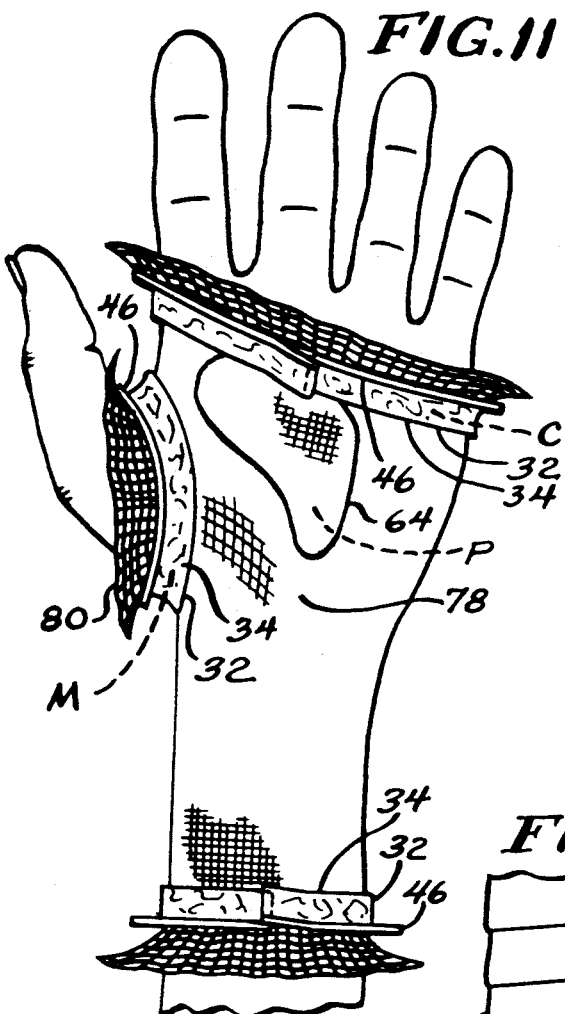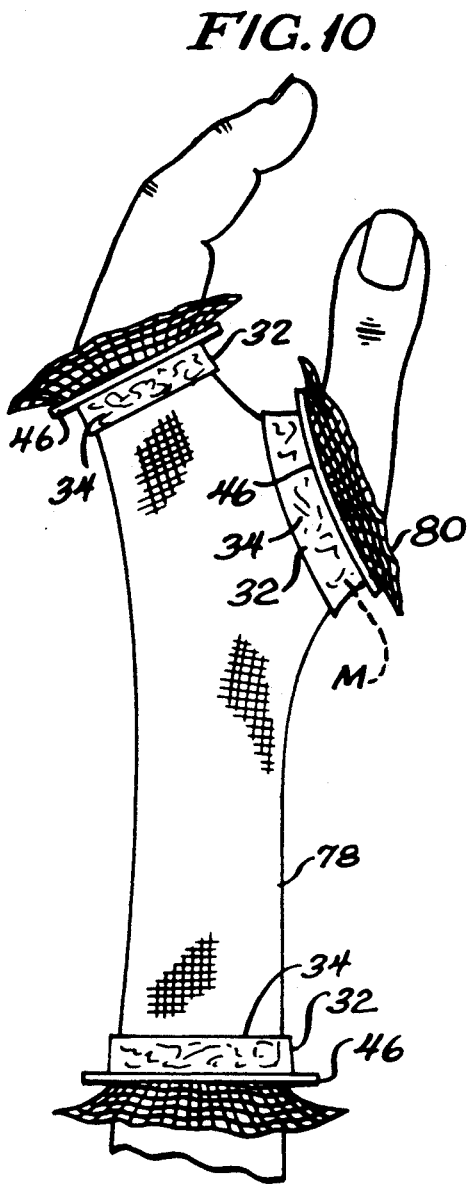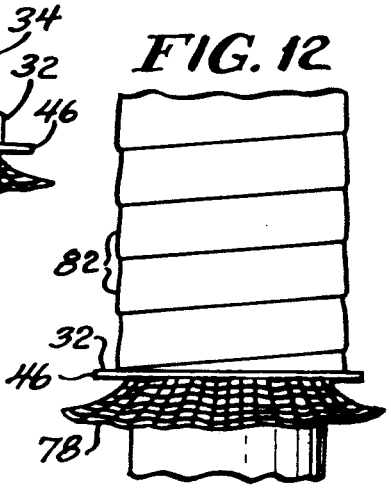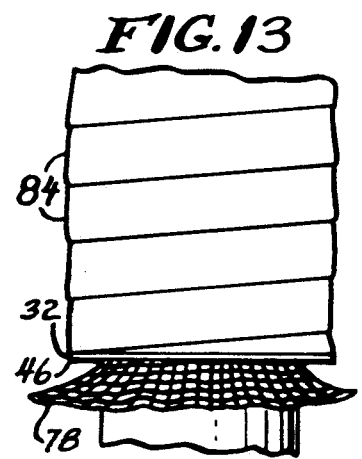

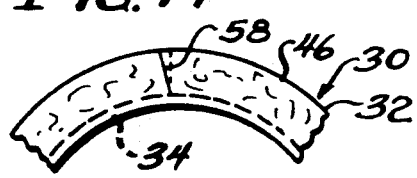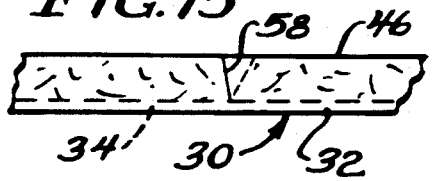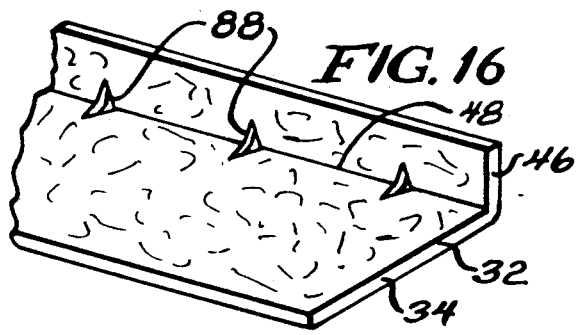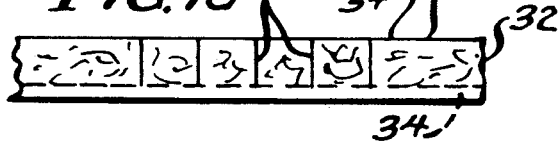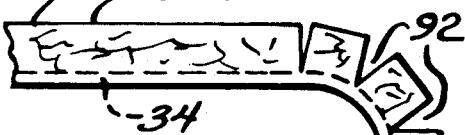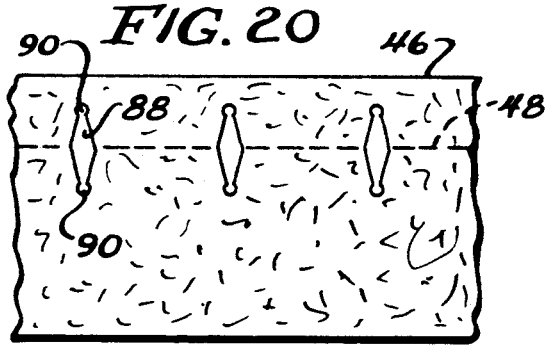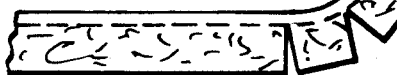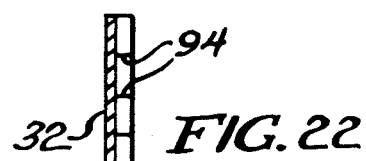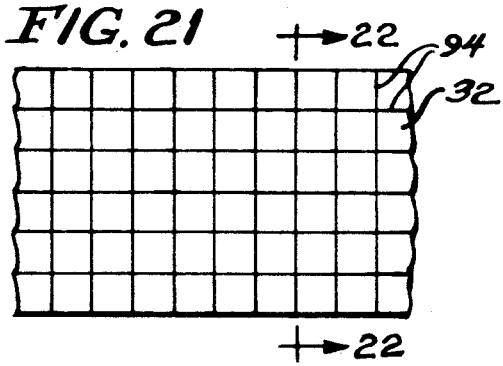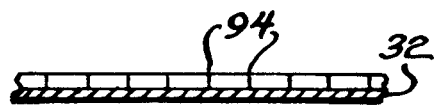

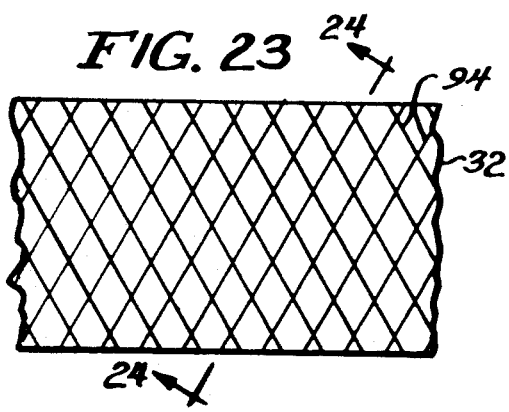
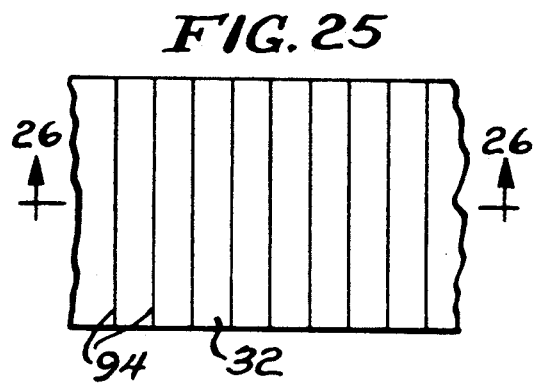
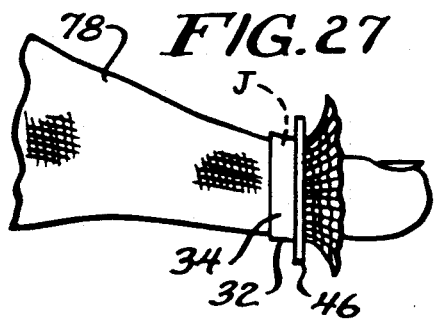
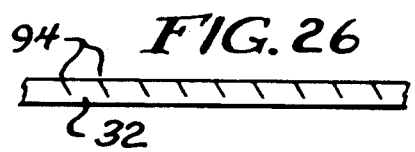
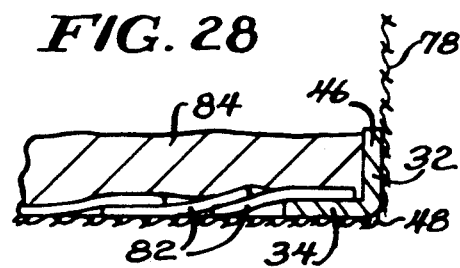
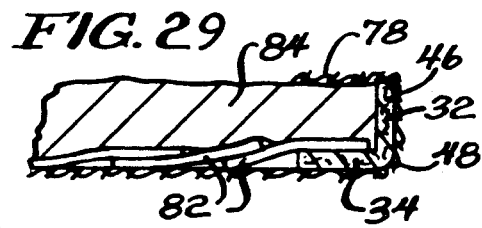

CAST PADDING

This is a continuation of application Ser. No. 890,555, filed Jul. 30, 1986 now abandoned.

BACKGROUND OF THE INVENTION

The present invention relates to casts, and more particularly to padding for such casts.

Fairly standard procedures have been used by physicians for many years to form a cast on a patient's extremity. Such procedures have been commonly accepted with little afterthought, since there have been few significant advances in the field for a long time which would present viable alternatives, except for a padding disclosed in U.S. Pat. No. 4,479,490. However, as discussed below, the current practice in such matters is deficient in many respects.

Thus, in the case of an arm cast, a sleeve of tubular knit, two-way stretch material, termed stockinette, is cut to length for placement over the patient's arm and hand, and an opening is cut in a side of the sleeve to receive the patient's thumb. The stockinette material defines the inside of the finished cast to provide a comfortable surface for the patient. Next, an elongated strip of sheet wadding or cast padding, which may be hereinafter termed "wadding", is wound in a helical and circular fashion about the patient's arm and hand over the stockinette material. Typically, the wadding may be wrapped in about three layers, and both the stockinette material and wadding initially extend beyond the desired distal border of the cast. The wrapped sheet wadding provides padding for the patient beneath plaster of the finished cast. However, when the wadding is wrapped about the patient's thumb, two unwrapped triangular regions frequently remain open on the front and back of the hand, termed the "intern's triangle", due to the difficulty of wrapping the wadding in this region of the hand. Further, the stockinette material does not extend along the thumb.

An elongated strip of plaster is then wrapped over the sheet wadding to form the outer part of the cast. At this time, a number of difficulties arise in the procedure. First, the plaster is permitted to contact the patient's skin through the intern's triangles formed by the wadding, resulting in discomfort and possible cutting of the skin as the patient moves his thumb in the cast during healing. Second, as the plaster is wrapped about the patient's thumb, the plaster itself may form open intern's triangles on the front and back of the hand resulting in a region of weakness in the final cast which extends between the apices of the opposed triangles.

Next, it is extremely desirable to immobilize the hand into a position of function by the cast while maintaining the transverse metacarpal arch in the hand. Generally speaking, the desired position of function may be visualized as the configuration assumed by the hand while grasping a ball the size of a small grapefruit. In this position, the hand may be immobilized for extended periods of time without contractures occurring in the fingers and thumb. Further, by maintaining the transverse metacarpal arch, the thumb is placed into a position opposing the little finger to prevent loss of function between the fingers and thumb. However, in order to accomplish this result in the past, it has been necessary for the physician to depress the plaster in the palm as it sets by applying continual pressure with the thumb against the wet plaster into the palmar depression or recess, i.e., the low area of the hand intermediate the group of muscles at the base of the thumb (thenar eminence) and the eminence proximal the base of the little finger (hypothenar eminence). When the cast finally sets, a depression of the cast is formed in the palmar recess to maintain the transverse arch, but at the cost of time and inconvenience to the physician.

Further, as the plaster is wrapped, the plaster layers form a tapered or feathered distal end which must be removed from the cast, since the end would otherwise break apart during use of the cast. Hence, the physician must wait until the cast sets, and then trim the plaster and sheet wadding generally along the location of the distal palmer crease in the hand. Next, the physician must obtain additional wet plaster, place it over the tacky plaster adjacent the distal trimmed edge, turn a distal end section of the stockinette material over onto newly wet plaster and place further wet plaster over the turned end section of the stockinette material in order to finish the distal end of the cast. It is apparent that such a procedure causes a great deal of inconvenience to the physician accompanied by loss of time. Even when trimmed, the cast may be thinner than desired at the distal end. Further, it is noted that the stockinette material does not extend along the thumb, which precludes finishing of the plaster around the thumb in this manner. Hence, the wadding may hang out of the cast in this area, and due to a natural tendency for some patients to pull out the wadding, the cast may eventually become loose. Similar procedures are utilized to form a cast on the patient's foot. In particular, it is necessary to trim and finish the distal end of the cast.

A cast padding for solving these problems is disclosed in U.S. Pat. No. 4,479,490, incorporated herein by reference. Although this cast padding has been found satisfactory, it is desirable to more easily make the padding conform to various sizes of the patient.

SUMMARY OF THE INVENTION

A principal feature of the present invention is the provision of improved cast padding for use in forming a cast on a patient.

The article of the invention comprises, an elongated strip of porous material having a base portion and a raised edge portion extending from a line of juncture with the base portion.

A feature of the present invention is that the strip may be cut to length and then placed about the patient.

Thus a feature of the invention is that the strip readily conforms to different sizes of patients.

Another feature of the invention is that wadding and casting materials may be wrapped to the edge portion which serves as a barrier.

A further feature of the invention is the provision of a pad for placement in the palmar recess to maintain the transverse metacarpal arch after formation of the cast.

Still another feature of the invention is that the padding eliminates the necessity of trimming the distal end of the plaster and wadding during formation of the cast.

A feature of the invention is that the padding eliminates weak spots in the cast adjacent the thumb on the front and back of the hand.

Still another feature of the invention is that outer sections of an inner stockinette material may be turned over the plaster at the ends of the padding.

Thus, another feature of the invention is that the padding facilitates finishing the cast without the necessity of obtaining additional plaster for placement over an end of stockinette material in the cast.

A feature of the invention is that the padding may be constructed in a simplified manner and at a reduced cost.

Yet another feature of the invention is that the padding simplifies formation of the cast.

A further feature of the invention is the provision of methods for forming a cast.

A feature of the invention of the provision of a preformed adjustable strip of padding for placement about the thumb.

Further features will become more fully apparent in the following description of the embodiments of this invention and from the appended claims.

DESCRIPTION OF THE DRAWINGS

In the drawings:

FIG. 1 is a perspective view of a strip of padding according to the present invention;

FIG. 2 is an end view of the strip of FIG. 1;

FIG. 3 is an end view of a padding strip in a modified form;

FIG. 4 is a plan view of the strip formed into a roll;

FIG. 5 is a perspective view of an adjustable preformed padding strip for the thumb;

FIG. 6 is a sectional view taken substantially as indicated along the line 6—6 of FIG. 5;

FIG. 7 is a plan view of the strip of FIG. 5;

FIG. 8 is a plan view of a pad for the palmar recess;

FIG. 9 is a sectional view taken substantially as indicated along the line 9—9 of FIG. 8;

FIG. 10 is a side elevational view of the padding strips as applied to the hand and arm;

FIG. 11 is a front elevational view of the padding strips and pad as applied to the patient's hand and arm;

FIG. 12 and 13 are fragmentary elevational views showing wadding and a cast material applied to form the cast;

FIGS. 14–25 show alternate embodiments of the padding strips, with FIGS. 22, 24, and 26 being fragmentary sectional views of FIGS. 21, 23, and 25, respectively;

FIG. 27 is a side elevational view of a padding strip as applied to a patient's foot; and FIGS. 28 and 29 are fragmentary sectional views showing completion of the cast.

DESCRIPTION OF THE PREFERRED EMBODIMENTS

Referring now to FIGS. 1 and 2, there is shown an article 30 for use in making a cast on a patient. The article 30 comprises an elongated strip 32 of porous padding material having a base portion 34. The base portion 34 includes an inner portion 36, an outer edge 38, an upper surface 40, and a lower surface 42, with a suitable adhesive 44 being disposed on the lower surface 42.

The strip 32 has a raised edge portion 46 extending outwardly from the inner portion 36 at a fold line 48 defining a line of juncture between the base portion 34 and edge portion 46, such that the strip 32 is preferably of one-piece construction. The edge portion 46 has an inner surface 50 facing in the direction of the base portion 34, an opposed outer surface 52, and an outer edge 54.

In one form, as shown in FIG. 2, the base portion 34 has a uniform thickness. However, as shown in FIG. 3, the base portion 34 may be tapered from the fold line 48 to the outer edge by skiving the base portion 34. The strip 32 is constructed from a porous material, such as felt, to permit breathing through the strip 32 when formed in the cast. A stiffening material, such as starch, may be applied to the strip 32 to obtain proper orientation of the edge portion 46.

As shown in FIG. 4, the strip 32 may be wound into a roll 56, and the strip 32 may be unwound from the roll 56 and cut to a suitable length for making the cast. With reference to FIG. 14, if the strip 32 is wound into the roll, the edge portion 46 may have oblique slits 58 such that adjacent portions of the slits 58 overlap when the strip 32 is formed into a straight configuration, as shown in FIG. 15, for conformability of the raised edge portion 46.

A preformed article 30 comprising an annular strip 32 for the thumb is shown in FIGS. 5–7, in which like reference numerals designate like parts. The strip 32 has an edge portion 46 disposed at an acute angle to a base portion 34 along a fold line 48. The strip 32 has a pair of opposed ends 60 and 62 located adjacent each other in the preformed strip 32. During the formation of the cast, the ends 60 and 62 may be overlapped or spaced in order to provide adjustment for different sizes of thumbs.

A pad 64 for the palmar recess in forming the cast is shown in FIGS. 8 and 9. The pad 64 has a first arcuate portion 66 at one end of the pad 64, and a second arcuate portion 68 at the other end of the pad, with the second arcuate portion 68 being directed outwardly from the first arcuate portion 66. The pad 64 is tapered from a central portion 70 toward an outer edge 72 of the pad 64, such as by skiving the pad 64, with the pad 64 having adhesive 74 on the tapered side of the pad 64. The pad 64 has a release sheet 76 of suitable type covering the adhesive 74, with the release sheet 76 being removed at the time of use of the pad 64 to expose the adhesive 74.

The formation of a cast for the hand will be discussed in connection with FIGS. 10-13, 28, and 29. First, as shown in FIGS. 10 and 11, a tubular open mesh fabric 78, such as stockinette, is placed over the arm and hand, with the fabric 78 having a tubular side extension 80 for the thumb. Next, the pad 64 is adhered to the fabric 78 in the region of the palmar recess P, and the preformed annular strip of FIGS. 5-7 is placed and adjusted on the thumb around the base of the first metacarpal M of the patient's hand. A strip 32 of FIGS. 1-3 is cut to length, and is placed around the patient's hand adjacent the distal palmar crease C, with opposed ends of the strip 32 being slightly spaced or overlapped, as desired. Another strip 32 of FIGS. 1-3 is cut to length, and is placed around the patient's arm proximal the hand, with opposed ends of the strip 32 being slightly spaced or overlapped as desired. The adhesive on the base portions of the strips 32 maintain the strips 32 on the fabric 78. However, if desired, the adhesive may be placed on the fabric 78 at the appropriate locations, and strips 32 without adhesive could be adhered to the adhesive on the fabric 78. Alternatively, the strips 32 could be secured to the fabric 78 prior to placement of the fabric 78 on the hand and arm.

Next, with reference to FIG. 12, an elongated sheet 82 of a known wadding material is wrapped over the fabric 78 against the edge portions 46 of the placed strips 32. As shown in FIG. 13, a sheet 84 of cast material, such as plaster or fiberglass, is then wrapped over the wadding sheet 82 against the raised edge portions 46 of the strips 32. As shown in FIGS. 28 and 29, ends of the fabric 78 are placed over the raised edge portions 46 of the strips 32 into the cast material 84 adjacent the edge portions 46 to complete the cast.

The formation of a cast for the distal part of the foot is described in connection with FIG. 27, in which like reference numerals designate like parts. A tubular portion of open mesh fabric 78, such as stockinette, is placed on the foot. A strip 32 of cast padding as shown in FIGS. 1-3 is then cut to length, and is adhered to the fabric 78 in the region of the metatarsophalangeal joint J proximal the toes. The cast is finished, as previously described, by sheets of wadding and cast material, and by placing an end of the fabric 78 into the cast material.

Although the article 30 has been primarily described in connection with formation of casts for the hand and foot, it will be understood that the article 30 may be used to make a cast on any appropriate part of the patient's body, particularly the extremities.

According to the present invention, the cast is formed in a simplified manner by cutting the strips 32 of cast material to the appropriate length, and placing them on the patient. The strips 32 may be constructed at a reduced cost in a simplified manner. The wadding and cast material may easily be wrapped to the edge portions 46 of the strips 32 which provide a barrier against which the wadding and cast material may be wrapped. The wadding and cast material may be applied with uniform thickness in the cast, and the strips 32 eliminate the necessity of trimming the ends of the plaster and wadding during formation of the cast. The strip 32 eliminates weak spots in the cast adjacent the thumb on the front and back of the hand. The outer ends of the fabric may be turned over the cast material which eliminates the necessity of obtaining additional plaster for placement over the ends of the fabric to finish the cast. The strips 32 also eliminate the "intern's triangle" adjacent the thumb. Also, the pad 64 maintains the transverse metacarpel arch by the cast. In the event that a fiberglass cast material is utilized to form the cast, the strips 32 prevent sharp edges of the cast which otherwise might cut the skin. Also, the strips 32 prevent shrinking of fiberglass cast material to prevent compression of the cast material against the patient.

An alternative embodiment of the strip 32 is shown in FIGS. 16 and 17, in which like reference numerals designate like parts. In this embodiment, the strip 32 may have spaced openings 88, such as in the shape of diamonds, along the fold line 48, with opposed ends of the openings 88 being located on opposed sides of the fold line 48. As shown on FIG. 17, the openings 88 close when the strip 32 is placed in a curved configuration for improved conformability of the strip 32. Also, the openings 88 permit formation of a small or large circumference without the edge portion 46 moving up or down. As shown in FIG. 20, the diamond shaped openings 88 may have circular openings 90 at opposed ends of the openings 88 to help maintain the edge portion 46.

As shown in FIGS. 18 and 19, the edge portion 46 of the strip 32 may have slits 92 extending from the outer edge 54 to the fold line 48, such that parts of the edge portion 46 separate from each other, as shown in FIG. 19, when the strip 32 is curved for improved conformability of the strip 32 to the patient's body.

With reference to FIGS. 21-26, the strips 32 may have slits 94 extending from one surface of the strips 32 part way through the strips 32 in order to make it easier to adapt the strips 32 to the various curves, bumps and depressions in the patient s extremity. As shown in FIGS. 21 and 22, the slits 94 may be perpendicular to each other and to the outer surface of the strips 32 to form a pattern of squares. With reference to FIGS. 23 and 24, the slits 94 may be perpendicular to the outer surface of the strip 32 and may cross each other to form a pattern of diamonds. As shown in FIGS. 25 and 26, the slits 94 may be oblique to the outer surface of the strips 32, and may form a pattern of parallel lines.

The foregoing detailed description is given for clearness of understanding only, and no unnecessary limitations should be understood therefrom, as modifications will be obvious to those skilled in the arts.

I claim:

1. A method of forming a cast on a patient's foot, comprising the steps of:
   placing an open mesh fabric material on the patient's foot;
   placing an elongated strip of porous material compatible with the cast material, said strip having a base portion and a raised edge portion around the patient's foot in the region of the metatarsophalangeal joint proximal the toes;
   wrapping a sheet of wadding around the patient's foot to the raised edge portion; and
   wrapping a cast material around the patient's foot to the raised edge portion.

2. The method of claim 1 including the step of placing an end of the fabric material over the raised edge portion into the cast material adjacent the raised edge portion.

3. The method of claim 1 including the step of adhering the strip to the fabric material.

4. A method of forming a cast on a patient's hand comprising the steps of:
   placing an open mesh fabric material on the patient's hand and arm and along a portion of the patient's thumb;
   placing an elongated strip of porous material compatible with the cast material, said strip having a base portion and a raised edge portion around the patient's hand adjacent the distal palmar crease;
   placing an elongated strip of porous material compatible with the cast material, said strip having a base portion and a raised edge portion around the patient's arm proximal the hand;
   placing an elongated strip of porous material compatible with the cast material, said strip having a base portion and a raised edge portion around the base of the first metacarpal of the patient's hand;
   wrapping a sheet of wadding around the patient's hand and arm between the raise edge portions of the strips; and
   wrapping a cast material around the patient's hand and arm between the raised portions of the strip.

5. The method of claim 4 including the step of placing ends of the fabric material over the raised edge portions into the cast material adjacent the raised edge portions.

6. The method of claim 4 including the step of adhering the strips to the fabric material.

7. The method of claim 4 including the step of placing a tapered pad against the fabric material in the region of the palmar recess.

8. An article for use in making and becoming a part of a cast on a patient, comprising:
   an elongated strip of porous material compatible with material used to make the cast, said strip having a base portion including an inner portion, an outer edge, an upper surface, and a lower surface, and a generally planar edge portion extending outwardly from the inner portion at a line of juncture between the base portion and edge portion, said edge portion having an inner surface facing the base portion, an opposed outer surface, and terminating in an outer edge in the generally planar edge portion, said strip when positioned to form the end portion of a cast becoming a part thereof and being compatible with the material forming the cast wherein the strip has a plurality of slits extending from a surface of the strip part way through the strip.

9. The article of claim 8 wherein the slits are generally perpendicular to said surface.

10. The article of claim 9 wherein the slits define a pattern of squares.

11. The article of claim 9 wherein the slits define a pattern of diamonds.

12. The article of claim 8 wherein the slits extend obliquely from said surface.

13. The article of claim 12 wherein the slits define a pattern of spaced parallel lines.

14. A cast for use on a patient, comprising:
an open mesh fabric having an inner portion and an end portion;
an elongated strip of porous material compatible with the cast material, said strip having a base portion with an outer edge, and a generally planar raised edge portion extending from a line of juncture between the base portion and edge portion, said strip being formed into an annular configuration, with said strip having a pair of opposed ends located adjacent each other in annular configuration with the edge portion terminating in an outer edge on the generally planar edge portion, said base portion being placed over the inner portion of the open mesh fabric;
a wadding material placed over the inner portion of the open mesh fabric and the base portion of the strip;
a cast material placed above the wadding material to a location against the edge portion of the strip, with the end portion of the open mesh fabric being placed over the edge portion of the strip into the cast material adjacent the edge portion.

15. A cast for use on a patient, comprising:
an open mesh fabric having an inner portion and an end portion;
an elongated strip of porous material compatible with the cast material, said strip having a base portion including an inner portion, an outer edge, an upper surface, and a lower surface, and a generally planar edge portion extending outwardly from the inner portion at a line of juncture between the base portion and edge portion, said edge portion having an inner surface facing in the direction of the base portion, an opposed outer surface, and terminating in an outer edge in the generally planar edge portion, said base portion being place over the inner portion of the open mesh fabric;
a wadding material placed over the inner portion of the open mesh fabric and the base portion of the strip; and
a cast material placed over the wadding material to a location against the edge portion of the strip, with the end portion of the open mesh fabric being placed over the edge portion of the strip into the cast material adjacent the edge portion.

* * * * *